United States Patent [19]

Haces

[11] Patent Number: 5,248,618

[45] Date of Patent: Sep. 28, 1993

[54] METHODS FOR GENERATING LIGHT WITH CHEMILUMINESCENT DIOXETANES ACTIVATED BY ANCHIMERIC ASSISTED CLEAVAGE

[75] Inventor: Alberto Haces, Gaithersburg, Md.

[73] Assignee: Life Technologies, Inc., Gaithersburg, Md.

[21] Appl. No.: 710,332

[22] Filed: Jun. 5, 1991

[51] Int. Cl.$^5$ .................. G01N 21/76; G01N 33/53; C12Q 1/44; C07D 303/00

[52] U.S. Cl. .................. 436/172; 435/7.72; 435/19; 435/21; 549/332; 549/510

[58] Field of Search .................. 436/172, 166, 800; 435/19, 21, 7.72; 549/332, 510

[56] References Cited

U.S. PATENT DOCUMENTS

| | | | |
|---|---|---|---|
| 4,857,652 | 8/1989 | Schaap | 549/510 |
| 4,931,569 | 6/1990 | Edwards | 549/221 |
| 4,956,477 | 9/1990 | Bronstein | 549/221 |
| 4,959,182 | 9/1990 | Schaap | 252/700 |
| 4,962,192 | 10/1990 | Schaap | 536/18.1 |
| 4,978,614 | 12/1990 | Bronstein | 435/21 |
| 5,094,939 | 3/1992 | Okada | 435/6 |

FOREIGN PATENT DOCUMENTS

| | | |
|---|---|---|
| 8930943 | 9/1989 | Australia . |
| 0384717 | 8/1990 | European Pat. Off. . |

OTHER PUBLICATIONS

A Copy of Notes Regarding The Bronstein v. Schaap Interferences, Aug. 15, 1984 Irena Bronstein.

"Failure of Benzene and Phenol to Serve as Substrates for the Peroxidatic Action of Catalase", Sichak, S. P. et al., *J. Toxicol. Environ. Health* 31(3):227-33 (1990).

Washburn and Dennis, "Novel General Approach for the Assay and Inhibition of Hydrolytic Enzymes Utilizing Suicide-Inhibitory Bifunctionally Linked Substrates (SIBLINKS): Exemplified by a Phosphilipase A$_2$ Assay," *J. Am. Chem. Soc.* 112(5):2040-2041 (1990).

Washburn and Dennis, "Suicide-Inhibitory Bifunctionally Linked Substrates (SIBLINKS) as Phospholipase A$_2$ Inhibitors," *J. Am. Chem. Soc.* 112(5):2042-2043 (1990).

DeHaas et al., "Purification and Properties of Phospholipase A from Porcine Pancreas," *Biochim. Biophys. Acta* 159:103-117 (1968).

*Primary Examiner*—Michael G. Wityshyn
*Assistant Examiner*—Ralph Gitomer
*Attorney, Agent, or Firm*—Sterne, Kessler, Goldstein & Fox

[57] ABSTRACT

Novel assay methods employing compounds which are chemically or enzymatically cleavable and which give rise to an intermediate which further decomposes by an intramolecular anchimeric displacement reaction which releases a signal producing species are disclosed. Also disclosed are probe hybridization assays employing the compounds of the invention employing thermostable enzymes which are not denatured by the hybridization conditions. Such signal producing species may include chemiluminescent dioxetanes and other colored products.

13 Claims, No Drawings

METHODS FOR GENERATING LIGHT WITH CHEMILUMINESCENT DIOXETANES ACTIVATED BY ANCHIMERIC ASSISTED CLEAVAGE

FIELD OF THE INVENTION

The invention relates to the use of substrates comprising a signal generating moiety and a chemically or enzymatically cleavable group which, when cleaved, causes the further cleavage of a chemical bond by anchimeric assitance to release a signal generating moiety.

BACKGROUND OF THE INVENTION

Anchimeric assisted acceleration of nucleophilic substitution reactions have been well documented (Lowry TH and Richardson KS (1976), *Mechanism and Theory in Organic Chemistry*, Harper and Row, New York, p. 272). For instance, it is well known that the rate at which phosphodiesters of ethylene glycol hydrolyze, compared with those phosphodiesters which do not have a glycol functionality, is much faster under the same experimental conditions (Westheimer FH (1968) Accounts of Chem. Res. 1:70). This rate acceleration is the result of an attack at the phosphorous atom by an "internal" nucleophile, the unprotected hydroxyl group of the glycol moiety (Scheme I).

Scheme I

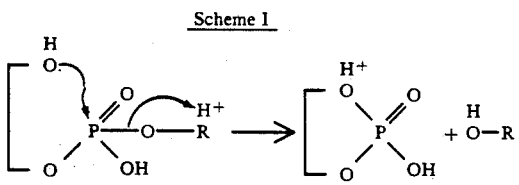

This hydroxyl group is not only more available due to its close proximity to the reactive site (high local concentration), but also requires a smaller amount of change of the order of the molecular arrangement or entropy. This in turn makes the activation energy of the reaction much lower, leading to a faster rate of reaction. This phenomenon occurs any time that a nucleophile is in close proximity to an electrophilic center (which possesses a leaving group) and both chemical entities may form a covalent or a transient bond. The electrophilic and nucleophilic centers may be part of an open chain or ring structure that requires a transannular reaction. In general, the product of the reaction has a ring arrangement of 3 to 6 members. Such ring sizes are optimal for a large acceleration rate of the leaving group displacement.

Washburn and Dennis, *J. Amer. Chem. Soc.* 112:2040-2041 (1990), ibid, 112:2042-2043 (1990), disclose an assay for phospholipase $A_2$ which employs a suicide-inhibitory bifunctionally linked enzyme substrate which is an irreversible enzyme inhibitor. For example, $PLA_2$-catalyzed hydrolysis of the sn-2 ester of 1-decanoyl-2-(p-nitrophenylglutaryl)phosphatidylcholine releases 1-decanoylphosphatidylcholine and p-nitrophenylglutarate which further reacts by an intramolecular nucleophilic displacement reaction to release p-nitrophenol and glutaric anhydride. The release of p-nitrophenol allows for the spectrophotometric detection of $PLA_2$. However, the release of glutaric anhydride or derivatives thereof from the corresponding substrate results in the suicide inhibition of $PLA_2$.

The enzymatic cleavage of chemical functionalities from substrates by enzymes is well known (Stryer L (1975) *Biochemistry*, W. H. Freeman & Co., San Francisco, p. 115). Thus, there exists a large variety of hydrolytic enzymes which cleave specific chemical bonds under appropriate conditions. For example, esterases cleave the carbonyl-oxygen bond of carboxylic esters and sometimes the carbonyl-sulfur bond of carboxylicthiol esters; phosphatases cleave esters of phosphoric acid and alcohols or phenols; and glycosidases cleave the glycosidic bonds of sugars. All these enzymes are highly specific for the type of bond which they are capable of cleaving.

High enzyme specificity, the compatibility with a large number of different substrate molecules, and the potential of producing large numbers of product molecules has led to the use of enzymes in various assay schemes. One example is the enzyme alkaline phosphatase which cleaves the substrate p-nitrophenyl phosphate to produce p-nitrophenol, an intensely yellow colored product. Thus, the presence of alkaline phosphatase in a solution or immobilized on a solid surface can be detected in the presence of p-nitrophenyl phosphate.

If the alkaline phosphatase is chemically bonded to a second molecule, the presence of this second molecule can be indirectly detected by testing for alkaline phosphatase. This procedure can be used to detect single stranded DNA molecules (a target) immobilized on a solid surface. This method of detection involves hybridization of the target DNA with another piece of DNA complementary to it (a probe), and to which alkaline phosphatase has been chemically bonded.

Methods for the assay of nucleic acids by hybridization are well known in the art. See, for example, U.S. Pat. No. 4,358,535; U.K. Patent Application Nos. GB 2,019,408 (1979) and GB 2,034,323 (1980); Klausner and Wilson, *Bio/Technology* 471 (1983); Reiser et al., *Biochem. Biophys. Res. Commun.* 85:1104-1112 (1978); Huang and Pagano, *Meth. Virol.* 6:457-497 (1977); Khandjian, *Molec. Biol. Rep.* 11:107-115 (1986); Hansen et al., *Anal. Biochem.* 162:130-136 (1987); Gootz et al., *Antimicrobial Agents and Chemother.* 28:69-73 (1985); Cunningham, *Anal. Biochem.* 128:415-421 (1983); Langdale and Malcolm, *Gene* 36:201-210 (1985); and Albrecht and Lazier, *J. Biochem. Biophys. Meth.* 9:215-220 (1984).

For this process to be efficient, the target/probe mixture has to be subjected to conditions (65° C. for several hours) which are detrimental to the alkaline phosphatase and will usually denature it. Thus, no signal or a very weak one might be obtained. Using milder conditions for the hybridization process often leads to higher desired signals, but also to increased background signal which reduces the sensitivity of the assay.

Enzymatically and chemically cleavable, chemiluminescent dioxetanes have been employed in various assays, including assays utilizing labeled DNA probes. See, for example, U.S. Pat. Nos. 4,987,614 and 4,959,182. U.S. Pat. No. 4,959,182 discloses compounds of the formula:

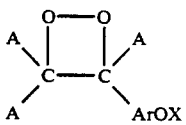

wherein ArOX is an aryl group having an aryl ring substituted with an X-oxy group. This group forms an unstable aryl oxide intermediate 1,2-dioxetane compound when triggered by removal of X by an activating agent. The unstable 1,2-dioxetane compound then decomposes and releases electronic energy to form light and two carbonyl containing compounds of the formulae

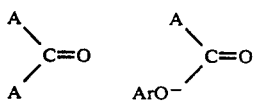

wherein A are passive organic groups which allow the light to be produced.

SUMMARY OF THE INVENTION

The invention relates to a method for generating light which comprises:

a. providing in a setting where the light is to be produced, a compound of the Formula (I)

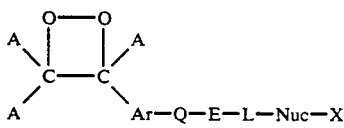

wherein Ar is an aryl group, Q is a heteroatom, E is an electrophilic group, L is a linking group of 1 to 5 atoms, Nuc is a nucleophilic group, X is an enzymatically or chemically cleavable group, and A are passive organic groups which allow the light to be produced;

b. activating the compound by cleaving the group X with an activating agent to give the intermediate having the Formula (II):

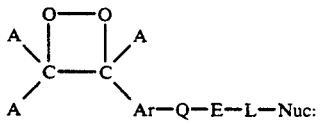

whereby the electron pair on the group Nuc thereafter attacks the electrophilic group E by anchimeric assistance to release the second intermediate having the Formula (III):

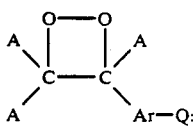

which is an unstable intermediate 1,2-dioxetane compound that decomposes and releases light.

The invention also relates to an assay method in which a member of a specific binding pair is detected by means of a signal producing moiety, which comprises: providing a compound having the Formula (IV):

Sig-E-L-Nuc-X    (IV)

wherein Sig is a signal producing moiety, E is an electrophilic atom, L is a linking group of 1 to 4 atoms, Nuc is a nucleophilic atom, and X is an enzymatically or chemically cleavable group;

b. activating the compound above by cleaving the group X to give the intermediate having the Formula (V):

Sig-E-L-Nuc:    (V)

wherein the electrophilic group E is thereafter attacked by the electron pair on the group Nuc: by anchimeric assistance to release the signal producing moiety and a compound having the Formula (VI):

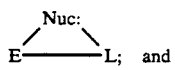

c. detecting the signal producing moiety.

The invention also relates to a method for detecting a nucleic acid by hybridization of the nucleic acid with a nucleic acid probe having an enzyme label or by hybridization of the nucleic acid with a nucleic acid probe which is capable of being enzyme labeled, and then generating a detectable signal by means of the enzyme label, the improvement which comprises:

a. providing a compound of the Formula (IV):

Sig-E-L-Nuc-X    (IV)

wherein Sig is a signal producing moiety, E is an electrophilic atom, L is a linking group of 1 to 4 atoms, Nuc is a nucleophilic atom, and X is an enzymatically or chemically cleavable group;

b. activating the compound by cleaving the group X with said enzyme label to give the intermediate:

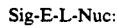

Sig-E-L-Nuc:    (V)

whereby the electron pair on the group Nuc: thereafter attacks the electrophilic group E by anchimeric assistance to release the signal producing moiety; and detecting the signal producing moiety.

DESCRIPTION OF THE PREFERRED EMBODIMENTS

The present invention is directed to a general method for the activation or "triggering" of chemical substrates to produce a detectable signal. The method employs substrates, especially 1,2-dioxetane substrates, which decompose in a two stage mechanism after the chemical or enzymatic bond cleavage. The initial intermediate formed by the enzymatic or chemical cleavage reaction further reacts by a nucleophilic intramolecular displacement reaction involving attack by the nucleophilic functional group released by the initial enzymatic or chemical cleavage reaction on a proximal electrophilic functional group which releases the signal producing species. The intramolecular displacement reaction gives rise to a 3- to 6-membered ring product. The second cleavage is greatly accelerated by the chemical phenomenon known as anchimeric assistance.

The compounds which may be used in the practice of the invention have the Formula (IV):

$$\text{Sig-E-L-Nuc-X} \qquad (IV)$$

wherein Sig is a signal producing moiety, E is an electrophilic atom, L is a linking group of 1 to 4 atoms, Nuc is a nucleophilic atom, and X is an enzymatically or chemically cleavable group;

Compounds having Formula (IV) may be cleaved with an enzyme to give the intermediate (V):

$$\text{Sig-E-L-Nuc:} \qquad (V)$$

wherein the electron pair on the group Nuc thereafter attacks the electrophilic group E by anchimeric assistance to release the signal producing moiety which may then be detected.

Preferably, the compound having the Formula (VI):

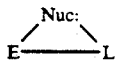 (VI)

which is produced by the anchimeric assisted cleavage reaction as well as the compounds having Formulae (V) and (VI) are not suicide inhibitors of the enzyme label. Examples of such suicide inhibitors are taught by Washburn and Dennis, supra, incorporated by reference herein, and include cyclic anhydrides such as glutaryl anhydride and succinic anhydride and the methylated derivatives thereof.

Preferred enzymes which may be used in the practice of the invention include esterases, acetylcholinesterase, acid and alkaline phosphatase, decarboxylases, lipases, phospholipases, catalases, glycosidase, galactosidase, glucosidase, xylosidase, fucosidase, mannoidase, thioglucosidase, amylase, peptidase, trypsin and chymotrypsin. Especially preferred is alkaline phosphatase which is employed extensively in enzyme-linked immunoassays and to label nucleic acid probes. Also preferred is phospholipase $A_2$.

Most preferably, the enzyme used in the practice of the invention remains active at a temperature of about 50°-70° C. and/or under the wash conditions typically employed in hybridization assays, e.g., in the presence of 2% SDS, 8M urea or 5M guanidine hydrochloride. An enzyme is considered thermostable if it has a half life of at least 5 hours at 60° C. Examples of such thermostable enzymes include natural and engineered enzymes such as phospholipase $A_2$, alkaline phosphatase from human milk which is completely resistant to heating at 65° C. (Nin-Nin Chuang, *Clinica Chimica Acta.* 169:165-174 (1987)), thermostable alkaline phosphatase from the sera which is stable at 65° C. (Nath and Saha, *Clinica Chimica Acta* 55:5-9 (1974)); bacterial thermostable α-amylase which is resistant to thermal inactivation at 75° C. (Lonsane and Ramesh, *Adv. Appl. Micro.* 35:1-56 (1990), Heinen and Lauwers, *Experientia* 77-89 (1976)); arginine decarboxylase from avocado fruit which has maximal activity at 60° C. (Winer et al., *Plant. Physiol.* 76:233-237 (1984)); β-galactosidase from a thermophilic Bacillus which has optimal activity at 75° C. (Griffiths and Muir, *J. Sci. Fd Agric.* 29:753-761 (1978)); α-glucosidase from the thermophile *Bacillus caldolyticus* C2 which shows optimal activity at 60° C. and which retains 100% of initial activity at 60° C. for 2 hr. (Krohn and Lindsay, *Curr. Microbio.* 22:133-140 (1991)); lipase from Pseudomonas sp. KWI-56 which retains 96% of initial activity after incubation at 60° C. for 24 hr. (Iitzumi et al., *Agric. Biol. Chem.* 54:1253-1258 (1990)); aminopeptidase from *Bacillus stearothermophilus* which is stable at 80° C. in the presence of cobalt ions (Gamal and Attia, *Zbl. Bakt II Abt.* 134:733-739 (1979); β-xylosidase from *Saccharum Officinarum* which slowly inactivates at 65°-75° C. (Chinen et al., *J. Biochem* 92:1873-1881 (1982)); lipase from Bacillus sp. A30-1, ATCC No. 53841 which retains 100% of activity at 60° C. for 2 hrs. (European Patent Application Publication No. 0 384 717). See also European Patent Application Publication No. 258 017, PCT Application Publication No. WO90 9436, European Patent Application Publication No. 384 717, European Patent Application Publication No. 305 216, U.S. Pat. No. 4,929,557, 4,970,158, 4,628,028, 4,861,718, and 4,480,036.

Thus, the invention is also directed to the use of thermostable enzymes in the methods of the invention wherein the reaction conditions require high temperatures and/or denaturing conditions. As discussed above, phospholipase $A_2$ is advantageously employed in methods for detecting DNA by hybridization which require the use of high temperatures and detergents which denature alkaline phosphatase. The present invention overcomes the problem of enzyme deactivation by employing a thermostable enzyme which is resistant to the hybridization wash conditions.

In the claimed method, the group X may be a saturated or unsaturated $C_{2-10}$ acyl group, a phosphate or phosphate ester groups, a saturated or unsaturated alkyl or aryl carboxyl groups, a glyceride, e.g. 3-phospho-1,2-diacyl glyceride, or a glycoside, e.g. beta-D-xyloside, beta-D-fucoside, 1-thioglucoside, beta-D-galactoside, alpha-D-galactoside, alpha-D-glucoside, beta-D-glucoside, alpha-D-mannoside, beta-D-mannoside, beta-D-fructofuranoside, beta-D-glucosiduronate, p-toluenesulfonyl-L-argininyl, p-toluenesulfonyl-L-lysyl, p-toluenesulfonyl-L-aspartyl, p-toluenesulfonyl-L-glutamyl, starch, or glycogen.

The group X may also be a carboxyl ester, a silyl ether, trityl, or a gamma-unsaturated radical.

In general, the group Ar is a chromophore which is capable of detection such as phenyl, naphthyl, anthracene, rhodamine, fluorescein, eosin, indolyl, coumarinyl, erythrosin, acridine, aciridine, stilbene, nitrobenzoxadiazoles, quinoline, acidoacridine, carbazole, fluorescent cyanines, carbocyanine, pyridinium salts, oxonaols, resorofins or derivatives thereof. Preferably, where the group Sig is a chemiluminescent dioxetane, the group Ar is phenyl, naphthyl, indolyl or coumarin.

The linking group L may be a 1 to 4 atom chain which may be substituted with a group which is compatable with the enzymatic cleavage reaction and the intramolecular anchimeric cleavage reaction. Such substituents include saturated or unsaturated $C_{1-24}$ alkyl, saturated or unsaturated $C_{1-24}$ acyloxy-substituted $C_{1-24}$ alkyl, saturated or unsaturated di-$C_{1-24}$ acyloxy-substituted $C_{1-24}$ alkyl, $C_{6-10}$ aryl or saturated or unsaturated $C_{1-24}$ alkyl substituted by phenyl, hydroxyphenyl, indolyl, mercapto, $C_1$-$C_4$ alkylthio, hydroxy, carboxy, amino, guanidino, imidazole or carbamyl. Particular compatible groups may be required for recognition by a particular enzyme.

Typical L groups include $C_{1-4}$ mono- and polymethylene groups as well as the corresponding ether, thioether and amino derivatives, e.g.—$(CH_2)_x$—O—$(CH_2)_y$—, —$(CH_2)_x$—S—$(CH_2)_y$—, and —$(CH_2)_x$—N-R—$(CH_2)_y$—, wherein x and y are 0-3 and $x+y=2$ or 3 and R is a saturated or unsaturated $C_{1-24}$ alkyl group or a saturated or unsaturated $C_{2-24}$ acyl group.

The group X may be removed by chemical or enzymatic means as required by the particular group X. In some cases, one equivalent of a chemical reagent such as fluoride ion is required or only a very small amount of an enzyme need be employed. The agents are described in detail in U.S. Pat. Nos. 4,959,182 and 4,978,614, the disclosures of which are incorporated by reference herein in their entirety. Such agents include acids, bases, salts, enzymes and other inorganic and organic catalysts. The agent used will depend on the conditions under which the stable 1,2-dioxetane is to be activated and how labile is the particular X group. Electron donors can be used to remove the group X include reducing agents such as borohydride salts as well as electrical sources of electrons.

Examples of the group X which may be cleaved by the enzymes listed above include acyl groups, phosphate and phosphate ester groups, alkyl and aryl carboxyl groups, 3-phospho-1,2-diacyl glyceride, beta-D-xyloside, beta-D-fucoside, 1-thioglucoside, beta-D-galactoside, alpha-D-galactoside, alpha-D-glucoside, beta-D-glucoside, alpha-D-mannoside, beta-D-mannoside, beta-D-fructofuranoside, beta-D-glucosiduronate, p-toluenesulfonyl-L-argininyl, p-toluenesulfonyl-L-lysyl, p-toluenesulfonyl-L-aspartyl, p-toluenesulfonyl-L-glutamyl, starch, and glycogen.

In addition to p-nitrophenol, other signal producing species which can be used in the practice of the claimed invention include biotin (reacting with labeled avidin), pyridoxal, 5-bromo-4-chloro-3-indolyl, 7-hydroxy-4-methylcoumarin, 5-aminosalicylic acid, o-phenylenediamine, 2,2′-azinodi(3-ethylbenzthiazoline)-6-sulfonic acid, resorofin, fluorescein isothiocyanate, umbelliferone, $\beta$-naphthol, imidazole, 3-pyridol, resorufin, rhodamine, phycoertherine, phyocyanin, allophyocyanin, o-phthaldehyde, fluorescamine, luminol, isoluminol, luciferin, luciferase, aequorin, p-hydroxyphenylpropionic acid, thermoatic acridinium ester, and chemiluminescent dioxetanes. See, for example, U.S. Pat. Nos. 4,931,223, 4,945,039, 4,950,588, 4,950,613, 4,952,707, 4,956,477 4,959,182, 4,962,192, 4,975,380, 4,983,779, 4,978,614, 4,996,143, and 5,013,827.

Examples of the group X which may be cleaved by chemical means include acyl groups which comprise carboxyl esters or amides, silyl ethers, trityl, and gamma-unsaturated radicals.

The group Nuc may be any atom which has an unshared electron pair after cleavage of the group X and which is capable of participating in an intramolecular displacement reaction on the electrophilic group E. Examples of Nuc are O, S, N, Se, and Ge, although other nucleophilic functional groups may employed.

The electrophilic group E may be any electrophile which is capable of forming an intermediate having Formula (III) and which will participate in a nucleophilic displacement reaction with Nuc. Examples of electrophiles E which may be used in the practice of the invention include carboxyl, carbonyl, methylene substituted by a leaving group, phosphate, carbonate, xanthate, sulfite, sulfonate, bisulfate and bisulfide groups.

Typical saturated and unsaturated acyl groups which may be employed in the practive of the invention include, but are not limited to, acetate, propionate, butanoate, pentanoate, hexanoate, heptanoate, octanoate, nonanoate, decanoate, palmitoyl, oleyl, myristoyl, and stearoyl groups. Also included within the scope of R groups include the 3-($C_2$-$C_{24}$ acyloxy)-substituted aforementioned acyl groups wherein the $C_2$-$C_{24}$ acyloxy groups include, but are not limited to, acetate, propanoate, butanoate, pentanoate, hexanoate, heptanoate, octanoate, nonanoate, deconoate, and dedecanoate groups.

Typical $C_1$-$C_{24}$ alkyl groups include methyl, ethyl, n-propyl, i-propyl, n-butyl, t-butyl, i-butyl, pentyl, hexyl, heptyl, octyl, nonanyl, decanyl, undecanyl, dodecanyl, tridecanyl, tetradecanyl, pentadecanyl, heptadecanyl, octadecanyl, nonadecanyl, eicosanyl, heneicosanyl, docosanyl, tricosanyl, and tetracosanyl groups.

A sampling of the types of enzymes along with typical substrates that may be used in the present invention are presented in Scheme II. This list is not exhaustive; those of ordinary skill in the art may readily identify other substrate-enzyme combinations that may be used in the practice of the present invention. In Scheme II, the bond of the substrate broken by the enzyme is indicated by the broken line (- - -). In cases where an enzyme is listed more than once, the several substrates are presented or more than one bond may be attacked by the enzyme.

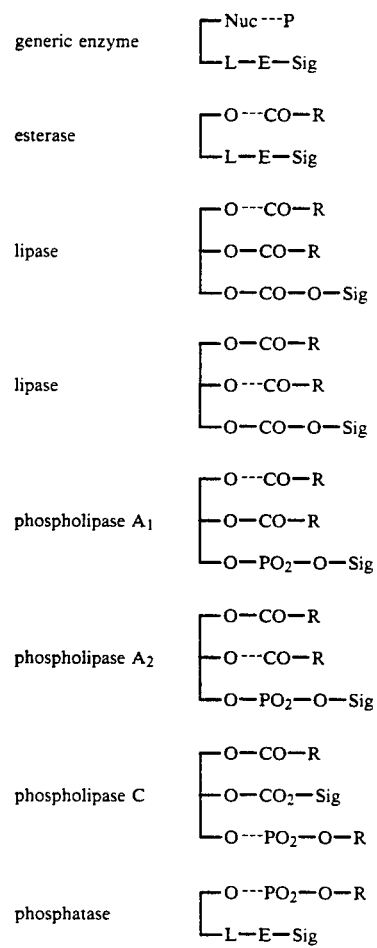

-continued
Scheme II catalase
$$\begin{bmatrix} O---OH \\ L-E-Sig \end{bmatrix}$$

glycosidase
$$\begin{bmatrix} O---sugar \\ L-E-Sig \end{bmatrix}$$

galactosidase
$$\begin{bmatrix} O---galactose \\ L-E-Sig \end{bmatrix}$$

glucosidase
$$\begin{bmatrix} O---glucose \\ L-E-Sig \end{bmatrix}$$

xylosidase
$$\begin{bmatrix} O---xylose \\ L-E-Sig \end{bmatrix}$$

fucosidase
$$\begin{bmatrix} O---fucose \\ L-E-Sig \end{bmatrix}$$

mannosidase
$$\begin{bmatrix} O---mannose \\ L-E-Sig \end{bmatrix}$$

thioglucosidase
$$\begin{bmatrix} S---glucose \\ L-E-Sig \end{bmatrix}$$

amylase
$$\begin{bmatrix} O---starch \\ L-E-Sig \end{bmatrix}$$

amylase
$$\begin{bmatrix} O---glycogen \\ L-E-Sig \end{bmatrix}$$

peptidase
$$\begin{bmatrix} NH---CO-R \\ L-E-Sig \end{bmatrix}$$

trypsin
$$\begin{bmatrix} NH---CO-C-NH-SO_2-p-C_6H_4CH_3 \text{ (p-tolyl)} \\ \phantom{NH---CO-}(CH_2)_3-NH-C^+(NH_2)_2 \text{ (arginyl)} \\ L-E-Sig \end{bmatrix}$$

trypsin
$$\begin{bmatrix} NH---CO-C-NH-SO_2-p-C_6H_4CH_3 \text{ (p-tolyl)} \\ \phantom{NH---CO-}(CH_2)_4-NH_3^+ \text{ (lysyl)} \\ L-E-Sig \end{bmatrix}$$

chymotrypsin
$$\begin{bmatrix} NH---CO-C-NH-SO_2-p-C_6H_4CH_3 \text{ (p-tolyl)} \\ \phantom{NH---CO-}CH_2-CO-O^- \text{ (aspartyl)} \\ L-E-Sig \end{bmatrix}$$

chymotrypsin
$$\begin{bmatrix} NH---CO-C-NH-SO_2-p-C_6H_4CH_3 \text{ (p-tolyl)} \\ \phantom{NH---CO-}(CH_2)_2-CO-O^- \text{ (glutamyl)} \\ L-E-Sig \end{bmatrix}$$

decarboxylases
$$\begin{bmatrix} O---CO-O-R \\ L-E-Sig \end{bmatrix}$$

In Scheme II, R=H, alkyl, acyl, aryl, or the like for substrates cleavable with a decarboxylase.

The preferred compounds which may be used in the practice of the present invention are chemiluminescent dioxetanes having the Formula (I):

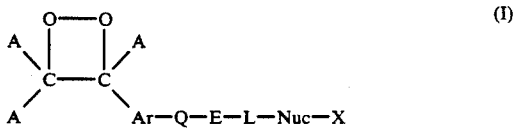

wherein Ar is an aryl group, Q is a heteroatom, E is an electrophilic group, L is a linking group of 2 to 5 atoms, Nuc is a nucleophilic group, X is an enzymatically or chemically cleavable group, and A are passive organic groups which allow the light to be produced. When the X group is removed by enzymatic or chemical cleavage, the following intermediate having Formula (II) is formed:

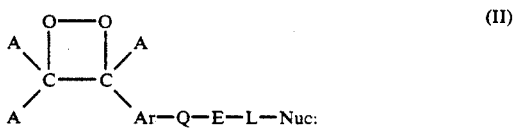

wherein the electron pair on the group Nuc thereafter attacks the electrophilic group E by anchimeric assistance to release the intermediate having Formula (III):

which is an unstable intermediate 1,2-dioxetane compound that decomposes and releases electronic energy to form light.

A particularly preferred compound has the Formula (VII):

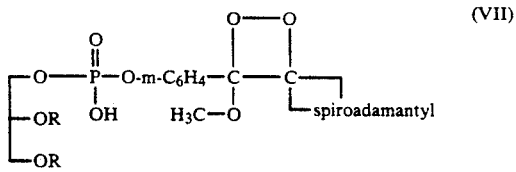

wherein R is a saturated or unsaturated $C_{1-24}$ acyl group; and said thermostable enzyme is phospholipase $A_2$. Also preferred is a compound having the Formula (VIII):

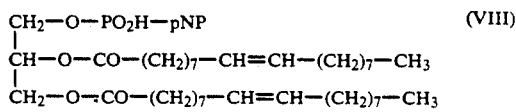

wherein pNP is para-nitrophenyl and wherein said thermostable enzyme is phospholipase $A_2$.

Scheme III depicts a particular substrate-enzyme combination and the use thereof in the methods of the present invention. The mechanism of anchimeric assisted cleavage to give the unstable dioxetane intermediate is shown when Sig is dioxetane.

Scheme III

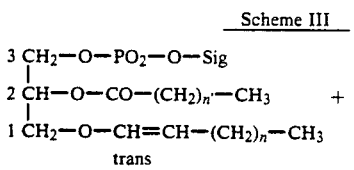

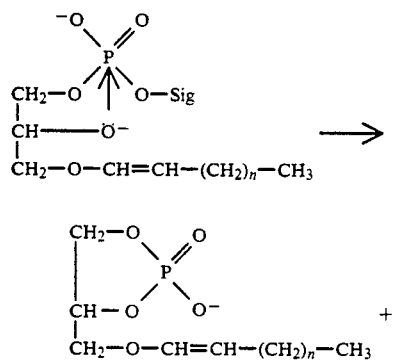

Scheme IV depicts the activation of a substrate with alkaline phosphatase which further decomposes by anchimeric assisted cleavage of a carbonate ester which is vicinal to a phosphate ester.

Scheme IV

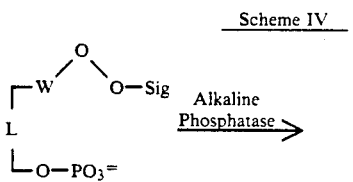

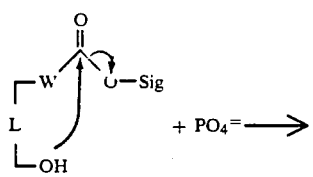

Analogously, an esterase can be used to release a hydroxyl group which is capable of entering into a further reaction to release an unstable dioxetane, wherein the esterase gives a result similar to when a phosphate is used to cleave a phosphate group (Scheme V).

Scheme V

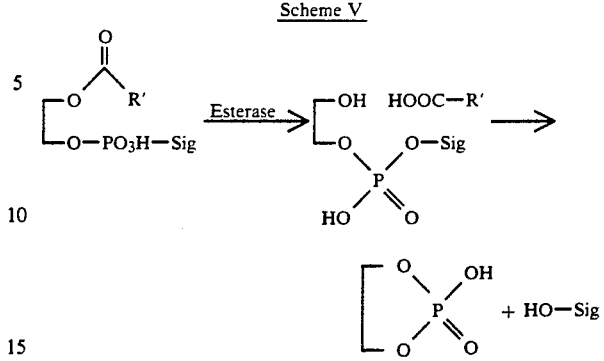

In addition, an esterase may be used to release a sulfhydryl group which is capable of a nucleophilic displacement reaction on a disulfide to give a colored product (Scheme VI)

Scheme VI

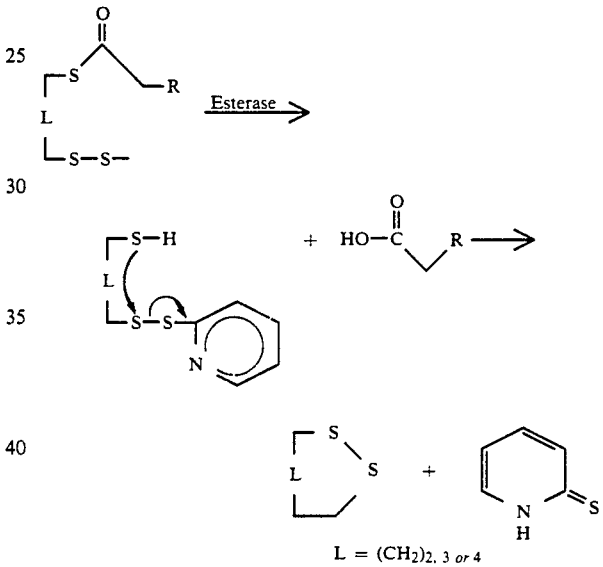

$L = (CH_2)_{2, 3 \text{ or } 4}$

As shown in Scheme VII, chemical triggering can also be used to release a nucleophile which participates subsequently in an intramolecular nucleophilic displacement reaction to give an activated dioxetane.

Scheme VII

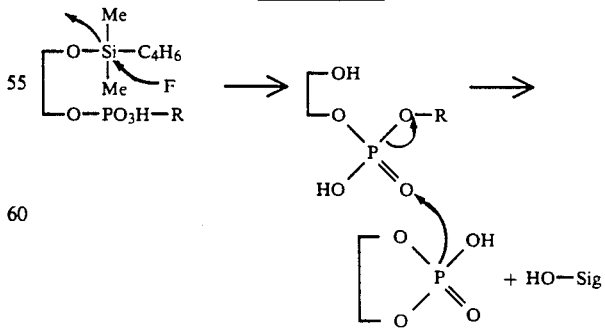

In contrast to the prior art, the chemical or enzymatic reagent cleaves a chemical bond which does not stabilize the dioxetane substrate. Thus, the release of the signal producing moiety, e.g. the 1,2-chemiluminescent dioxetane, occurs after *two* chemical bond have been cleaved in a two step sequential reaction. The second bond cleavage (the activation cleavage) which releases the signal producing moiety is mediated by anchimeric assistance.

Where there is a low reactivity of the particular enzyme under the conditions needed for the anchimeric assistnace to be optimal, one may first use the optimal conditions to cause the enzymatic cleavage and release of the nucleophilic group followed by a change of the conditions to those that favor anchimeric assistance. In general, depending on the method of triggering and the different activating agents, conditions can be found to optimize both reactions with no more than routine experimentation.

There exists a need for reporter-enzymes which are stable to heat and denaturing agents and that are capable of triggering signal generating substrates. The anchimeric assistance cleavage method allows for the selection of new enzymes which can be used to release signal generating moieties. For example, alkaline phosphatase has been used to activate a variety of dioxetane substrates in numerous applications. One such application is in the detection of small quantities of DNA immobilized on filter membranes by means of nucleic acid hybridization. This technique requires temperatures that are detrimental to the alkaline phosphatase enzyme, usually rendering it denatured and incapable of triggering the substrates. According to the present invention, a completely different enzyme such as phospholipase $A_2$, which is resistant to the hybridization conditions, can be used in place of alkaline phosphatase.

Phospholipase $A_2$ from porcine pancreas is stable at 85° C. in 2% SDS for long periods of time and is also resistant to high concentrations of chaotropic agents (8M urea, 5M guanidine hydrochloride) and is active at the pH range of 7-10. This enzyme is specific for particular types of substrates which are negatively charged, long fatty acid, charged phospholipids and, more specifically, for the ester bond on carbon 2 (the middle carbon) of the glycerol moiety of the phospholipid having Formula (IX).

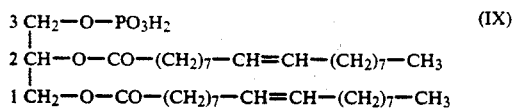

Small changes of the C-2 ester leads to total unreactivity with phospholipase $A_2$. On the other hand, phospholipase $A_2$ is not sensitive to changes on the phosphate ester functionality at C-3. Thus, a compound such as having Formula IX, in which the phosphate moiety has a p-nitrophenol group attached to it, is an acceptable substrate for the enzyme.

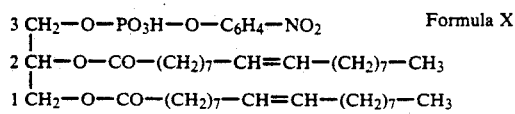

The C-2 alcohol compound having Formula XI is obtained from the compound of Formula X when the reaction is carried out at pH 7.5-8.0:

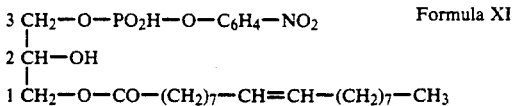

However, if the reaction is carried out at pH 8.5-10.0 (at pH greater than 10.5 the substrate slowly decomposes), the initial colorless product having Formula XI undergoes an internal reaction by which the C-2 hydroxyl displaces the p-nitrophenol group on the phosphate moiety to give a yellow colored signal. The latter process is an example of the anchimeric assistance effect described earlier. The first bond cleavage (the enzymatic cleavage) does not produce a signal. It is the secondary intramolecular displacement reaction which is responsible for releasing the signal-generating group. Furthermore, the final product of the reaction, p-nitrophenol, comes from the cleavage of a phosphate ester. However, phospholipase $A_2$ is an esterase. Thus, phospholipase $A_2$, an esterase, is acting as if it were a phosphatase.

The methods of the present invention may be applied to prior art assay substrates wherein a signal is generated after a leaving group is cleaved from the substrate. However, according to the present invention, a different enzyme is used to cleave a different chemical bond giving rise to an intermediate which further decomposes by anchimeric assistance to give an activated 1,2-dioxetane which then generates chemiluminescence. For example, the phosphatase-activated, fluorescent substrate used in Scheme VIII can be used in both the present invention and in certain prior art methods (U.S. Pat. No. 4,978,614, Table 1, scheme (4)). According to the prior art, the phosphate is removed by phospholipase D by hydrolysis of linkage A between the phosphate and the fluorophore (Formula XII). In the present invention, hydrolysis by phospholipase $A_2$ occurs between the C-2 ester and the glycerol moiety (linkage B, Formula XII) followed by anchimeric assistance cleavage of linkage A.

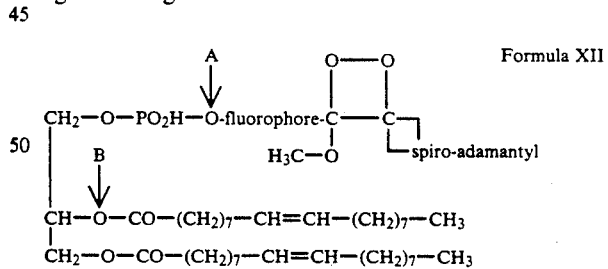

Scheme VIII

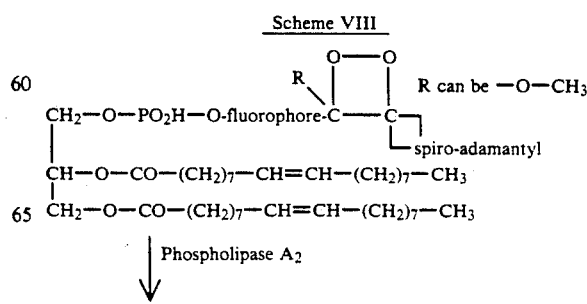

Scheme VIII -continued

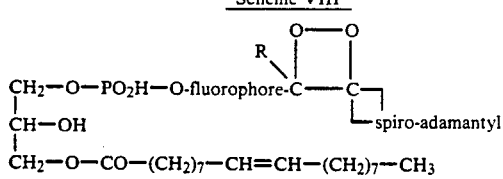

↓ Anchimeric Assistance Cleavage

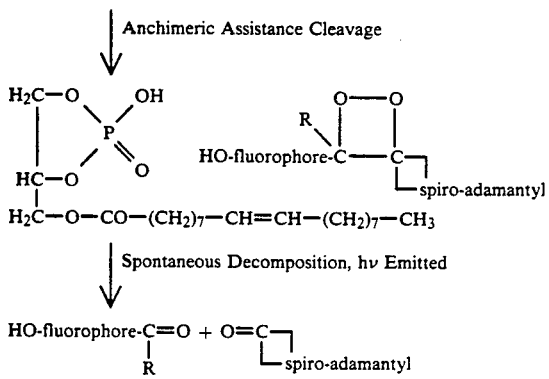

↓ Spontaneous Decomposition, hν Emitted

HO-fluorophore-C=O + O=C⟨spiro-adamantyl⟩
  |
  R

The moiety labeled "fluorophore" in Scheme VIII need not be, by itself, fluorescent (e.g. fluorescein). The term indicates only that the group is capable of absorbing energy to form an excited, i.e. higher energy, state, from which it emits light (hν). For example, it may be an o-phenyl group, as present in 3-(2'-spiro-adamantane)-4-methoxy-4-(3''-phosphophoryl-oxy)phenyl-1,2-dioxetane (compound 2c of U.S. Pat. No. 4,959,182; AMPPD of U.S. Pat. No. 4,978,614). AMPPD is a widely used, commercially available, luminescent label triggered by a phosphatase, commonly alkaline phosphatase. The light (hν) emitted need not be visible light, but may be ultraviolet or infrared, depending on the fluorophore chosen.

Chemiluminescence of the activated substrate may be enhanced by the addition of certain additives to the reaction. For example, the substrate may be admixed with a fluorescent compound and a surfactant to give a micelle. See U.S. Pat. No. 4,959,182. Such compositions exhibit enhanced chemiluminescence. Examples of such fluorescent compounds include any fluorescent compound having a lower energy for its singlet excited states compared to the excited state of the dioxetane product, e.g. any fluorescent dye, aromatic compounds including naphthalenes, anthracenes, pyrenes, biphenyls, acridine, coumarins, xanthenes, phthalocyanines, stilbenes, furans, oxazoles, oxadiazoles, and benzothiazoles. Preferably, the 1,2-dioxetane substrate is substituted with a C$_{8-20}$ carbon atom hydrocarbon chain or acyl group. Examples of surfactants which can be used in the practice of the invention are described in pages 1 to 18 of *Catalysis in Micellar and Macromolecular Systems*, Academic Press (1975). These include zwitterion, cationic (ammonium, pyridinium, phosphonium, sulfonium salts), anionic (sulfate, sulfonate, carboxylate salts), neutral (polyoxyethylene derivatives, cyclodextrins, long chain esters, long chain amides), and naturally occurring surfactants (lipids).

The preparation of and use of enzyme-triggerable 1,2-dioxetanes assays have been disclosed in numerous publications, including, but not limited to, European Patent Application Publication No. 254,051, U.S. Pat. Nos. 4,857,652; 4,931,223; 4,931,569; 4,952,707; 4,956,477; 4,959,182; 4,962,192; and U.S. Pat. No. 4,978,614, the disclosures of which are fully incorporated by reference herein.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLES

Example 1

Synthesis of PL-A$_2$ Chromogenic Substrate

The method for the synthesis of phospholipase A$_2$ (PL-A$_2$) chromogenic substrate that is useful in the present invention is diagrammed below in Scheme IX.

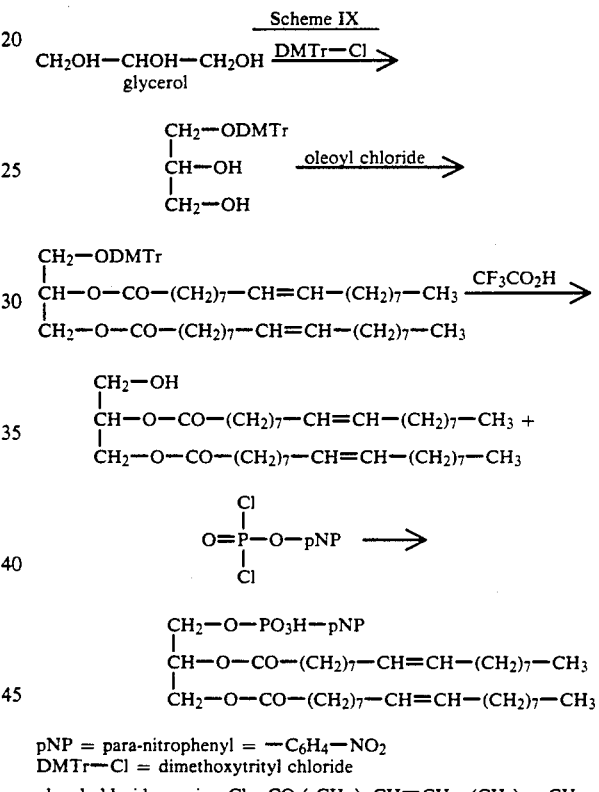

pNP = para-nitrophenyl = —C$_6$H$_4$—NO$_2$
DMTr—Cl = dimethoxytrityl chloride
oleoyl chloride = cis—Cl—CO—(CH$_2$)$_7$—CH=CH—(CH$_2$)$_7$—CH$_3$ A. Synthesis of 1-dimethoxytritylglycerol To a solution of glycerol (1 g, 10.8 mmol) in dry pyridine (60 mL) was added dimethoxytrityl chloride (3.3 g, 10.8 mmol) and dimethylaminopyridine (50 mg) as a catalyst. The resulting solution was stirred for 24 h at room temperature under argon. Water (100 mL) was added and the mixture extracted with methylene chloride (3×100 ml). The organic layer was washed with water (3×50 ml), dried (Na$_2$SO$_4$), and the solvent removed in vacuo. The residue was chromatographed on a short path silica gel column using, sequentially, methylene chloride and ethyl acetate as eluents to afford pure desired material (2.5 g, yield 60%). IR: (CH$_2$Cl$_2$) 3580, 2910, 1603, 1505 cm$^{-1}$ and H$^1$-NMR (CDCl$_3$) δ 1.6 (S, 1H), 2.05 (br S, 1H), 2.55 (S, 1H), 3.25 (m, 2H), 3.65 (m, 2H), 3.78 (S, 6H), 6.70 (d, 4H, J∼10 Hz), 7.15–7.45 (m, 8H).

B. Synthesis of 3-dimethoxytrityl-1,2-dioleoylglycerol

To a solution of 1-dimethoxytritylglycerol (620 mg, 1.57 mmol) in dry pyridine (15 mL) was added oleoyl chloride (1.45 mL, 1.31 g, 4.36 mmol) and the resulting mixture stirred for 18 h at room temperature. Cold (0° C.) water was added (50 mL) and the mixture stirred for 20 min followed by extraction with methylene chloride (3×50 ml). The organic layer was dried ($Na_2SO_4$) and the solvent removed in vacuo. The residue was passed through a short path silica gel column eluting with methylene chloride to afford, after solvent removal, clean desired product (1300 mg, yield 83%). IR: ($CH_2Cl_2$) 2940, 2870, 1740, 1603, 1505 cm$^{-1}$; $H^1$-NMR ($CDCl_3$) δ 0.88 (t, 6H, J~6.3 Hz), 1.28 (br S, 36H), 1.6 (br m, 8H), 2.0 (br s, 8H), 2.22 (t, 2H, J~7.8 Hz), 2.32 (t, 2H, J~7.8 Hz), 3.20 (d, 2H, J~5.6 Hz), 3.78 (S, 6H), 4.28 (m, 2H), 5.35 (m, 4H), 6.8 (d, 4H, J~10 Hz), 7.2–7.45 (m, 8H).

C. Synthesis of racemic 1,2-dioleoylglycerol

To a solution of 1-dimethoxytrityl-1,2-dioleoylglycerol (100 mg, 0.10 mmol) in methylene chloride (10 mL) was added an excess of trifluoroacetic acid. An instantaneous discharge of red color occurred and the mixture was let react for 10 min at room temperature. The organic reaction mixture was washed with water (5×10 mL), dried ($Na_2SO_4$), filtered, and the solvent removed in vacuo to about one third of the total volume. This solution was loaded on a silica gel column and eluted, sequentially, with methylene chloride and 5% ethyl acetate in methylene chloride. Evaporation of the appropriate fractions afforded pure desired product (50 mg, 80% yield). The $H^1$-NMR of this material was identical to that of a commercial sample of the L-α optically active isomer.

D. Synthesis of 1,2-dioleoyl-phosphatidyl-p-nitrophenol

To a solution of L-α-1,2-dioleoylglycerol (50 mg, 0.08 mmol) in dry pyridine (1 mL) was added p-nitrophenyl phosphorodichloridate (100 mg, 0.40 mmol) in dry pyridine (1 mL) and the resulting solution stirred overnight a room temperature under argon. Cold water (5 mL, 0° C.) was added and the mixture extracted with methylene chloride. The organic layer was washed with water (5×10 mL), dried ($Na_2SO_4$) and the solvent removed in vacuo to afford pure material (30 mg, 45% yield). IR: ($CH_2Cl_2$) 2950, 2890, 1740, 1603, 1520, 1500, 1460, 1355 cm$^{-1}$; $H^1$-NMR ($CDCl_3$) δ 0.9 (t, 6H, J~6.3 Hz), 1.25 (brS, 36H), 1.55 (brm, 8H), 2.0 (brs, 8H), 2.12–2.40 (br m, 4H), 4.05–4.40 (m, 4H), 5.3 (brS, 4H), 7.48 (br d, 2H), 8.15 (br d, 2H).

Example 2

Phospholipase $A_2$ Assay

To six out of twelve Eppendorff tubes each containing 200 μL of bicarbonate buffer (0.5M), 0.5% sodium dodecyl sulfate (SDS), and 0.25 mg 1,2-dioleoyl-phosphatidyl p-nitrophenol adjusted, pairwise, to pH 8.0, 8.5, 9.0, 9.5, 10.0, and 10.5 was added phospholipase $A_2$ (porcine) suspension in 3.2M ammonium sulfate (3 μL). To each of the remaining tubes was added 3.2M ammonium sulfate solution (3 μl/tube). The set of tubes was incubated at 37° C. for 30 minutes. Tubes at pH 8.5 and above containing enzyme showed varying degrees of yellow color, with the pH 8.5 tube palest and the pH 10.6 deepest. The control tubes showed faint yellow color (pH 10.0 tube) and clearly visible shade (pH 10.6 tube), the others were colorless. A visible spectrum scan showed a signal to noise ratio of 4.4, 8.0 and 2.5 for the pH 9.0, 9.5 and 10.0 tubes, respectively.

Example 3

Synthesis of PL-$A_2$ Chemiluminescent Substrates

Methods for the synthesis of phospholipase $A_2$ (PL-$A_2$) chemiluminescent substrates are diagrammed in Schemes X, XI, and XII. The substrates produced in Schemes X and XI are identical. The substrate produced in Scheme XII differs by having saturated palmitidyl R groups. Unsaturated hydrocarbons such as oleoyl groups are oxidized by the $O_2$ in the presence of the sensitox catalyst used in the last step of the reaction, thus, should be avoided.

Scheme X

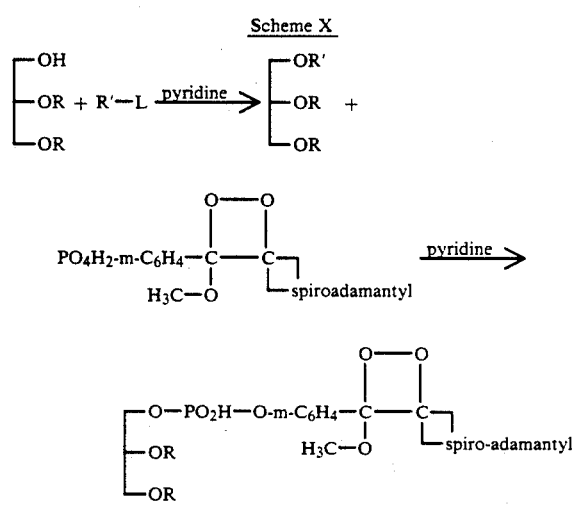

R = oleoyl
L = Cl, o-triflate
R' = tosyl, mesyl, o-triflate, $(n-C_4H_9)_3N^+-$

Scheme XI

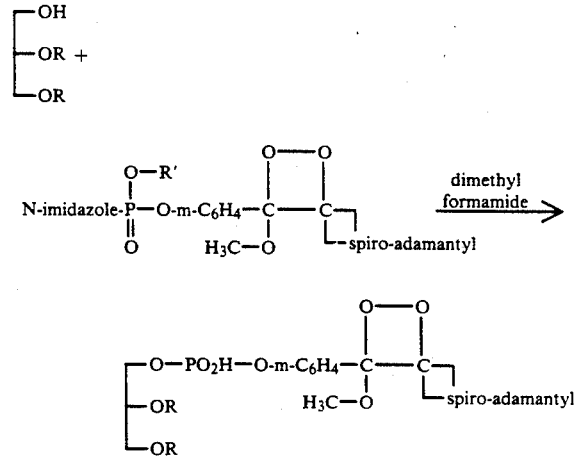

R = oleoyl
R' = $(n-C_4H_9)_3N^+-$

Scheme XII

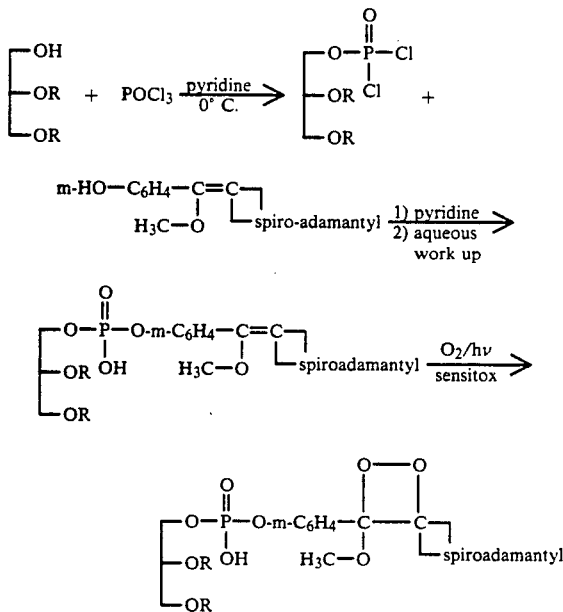

R = palmitoyl

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for generating light which comprises:
   (a) providing in a setting where the light is to be produced, a compound of the formula

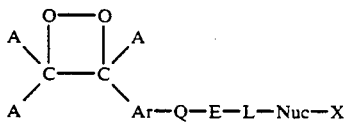

wherein Ar is an aryl group, Q is an oxygen atom, E is an electrophilic group, L is a linking group which is a $C_{1-4}$ mono- or polyethylene group, $-(CH_2)_x-O-(CH_2)_y$, $-(CH_2)_x-S-(CH_2)_y-$ or $-(CH_2)_x-NR-(CH_2)_y-$, wherein x and y are 0-3 and x+y=2 or 3 and wherein said linking group may be substituted by a saturated or unsaturated $C_{1-24}$ alkyl, saturated or unsaturated $C_{1-24}$ acyloxy-substituted $C_{1-24}$ alkyl, saturated or unsaturated di-$C_{1-24}$ acyloxy-substituted $C_{1-24}$ alkyl, $C_{6-10}$ aryl or saturated or unsaturated $C_{1-24}$ alkyl substituted by phenyl, hydroxyphenyl, indolyl, mercapto, $C_1-C_4$ alkylthio, hydroxy, carboxy, amino, guanidino, imidazole or carbamyl; Nuc is a nucleophilic group selected from the group consisting of O, S and N atoms; X is an enzymatically or chemically cleavable group, and A are passive organic groups which allow the light to be produced;

(b) activating the compound by cleaving the group X with an activating agent to give the intermediate:

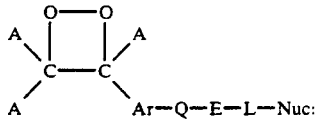

whereby the electron pair on the group Nuc: thereafter attacks the electrophilic group E by anchimeric assistance to release the second intermediate:

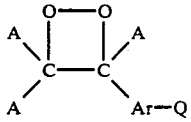

which is an unstable intermediate 1,2-dioxetane compound that decomposes and releases light.

2. The method of claim 1, wherein said group X is cleavable with an enzyme.

3. The method of claim 2, wherein said enzyme is catalase.

4. The method claim 2, wherein said enzyme is thermostable at a temperature of about 50°-70° C.

5. The method of claim 4, wherein said method of generating light is carried out during a hybridization assay and wherein said thermostable enzyme is stable during a washing step of the hybridization assay.

6. The method of claim 5, wherein said thermostable enzyme is phospholipase $A_2$.

7. The method of claim 1, wherein said group X is a saturated or unsaturated acyl group, a phosphate or phosphate ester group, a saturated or unsaturated alkyl or aryl-substituted carboxyl group, a glyceride or a glycoside.

8. The method of claim 7, wherein said glyceride is a 3-phospho-1,2-diacyl glyceride.

9. The method of claim 7, wherein said group X is a β-D-xyloside, β-D-fucoside, 1-thioglucoside, β-D-galactoside, α-D-galactoside, α-D-glucoside, β-D-glucoside, α-D-mannoside, β-D-mannoside, β-D-fructofuranoside, β-D-glucosiduronate, p-toluenesulfonyl-L-argininyl, p-toluenesulfonyl-L-lysyl, p-toluenesulfonyl-L-aspartyl, p-toluenesulfonyl-L-glutamyl, starch, or glycogen.

10. The method of claim 1, wherein the group X is a carboxyl ester, a silyl ether, trityl, or a gamma-unsaturated radical.

11. The method of claim 1, wherein the group Ar is a benzene, naphthalene, indolyl or coumarin ring.

12. The method of claim 1, wherein said compound has the formula:

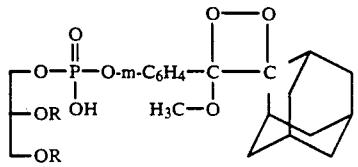

wherein R is a saturated or unsaturated $C_{1-24}$ acyl group.

13. The method of claim 1, wherein said compound has the formula:

21
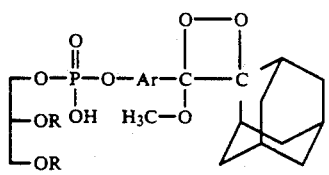
wherein R is a saturated or unsaturated $C_{1-24}$ acyl group.
* * * * *
22
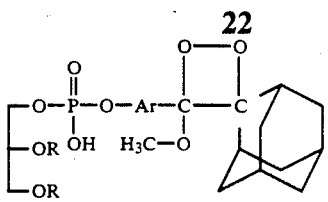
wherein R is a saturated or unsaturated $C_{1-24}$ acyl group.
* * * * *